United States Patent [19]
Sadhir et al.

[11] Patent Number: 5,707,871
[45] Date of Patent: Jan. 13, 1998

[54] METHOD AND KIT FOR TESTING POLYOLESTER LUBRICANTS USED IN REFRIGERANT COMPRESSORS

[75] Inventors: Rajender Kumar Sadhir, Murrysville; Margaret L. Fowkes, North Huntingdon, both of Pa.; Jeffrey Blaine Berge, Edina, Minn.

[73] Assignee: Thermo King Corporation, Minneapolis, Minn.

[21] Appl. No.: 605,309

[22] Filed: Feb. 7, 1996

[51] Int. Cl.$^6$ .................................................. G01N 33/30
[52] U.S. Cl. ........................... 436/61; 436/22; 436/23; 436/60; 422/60; 422/61; 422/59; 422/74; 422/75; 62/84; 62/125; 73/53.05
[58] Field of Search ................ 436/60, 61, 22, 436/23; 422/61, 59, 60, 74, 75; 62/84, 125; 73/53.05

[56] References Cited

U.S. PATENT DOCUMENTS

| | | | |
|---|---|---|---|
| 2,953,439 | 9/1960 | Elliott et al. | 436/61 |
| 3,193,356 | 7/1965 | Smith | 436/61 |
| 3,259,463 | 7/1966 | Feasley et al. | 436/61 |
| 3,510,260 | 5/1970 | Krawetz et al. | 436/61 |
| 3,808,149 | 4/1974 | Ellis et al. | 436/61 |
| 4,175,045 | 11/1979 | Timony | 252/56 S |
| 4,203,725 | 5/1980 | Snowden, Jr. et al. | 23/230 HC |
| 4,248,718 | 2/1981 | Vaughan | 252/33 |
| 4,288,402 | 9/1981 | Ellis | 422/61 |
| 4,604,227 | 8/1986 | Anzenberger, Sr. | 252/389.2 |
| 4,793,977 | 12/1988 | Morris | 436/61 |
| 4,962,234 | 10/1990 | Bandlish et al. | 564/384 |
| 5,242,469 | 9/1993 | Sakakibara et al. | 44/347 |
| 5,306,643 | 4/1994 | Sadhir et al. | 436/140 |
| 5,366,898 | 11/1994 | Hagstrom et al. | 436/60 |
| 5,377,496 | 1/1995 | Otto et al. | 436/61 |
| 5,494,597 | 2/1996 | Krevalis, Jr. et al. | 252/68 |
| 5,585,338 | 12/1996 | Beltzer | 508/518 |
| 5,593,957 | 1/1997 | Obara et al. | 508/501 |

FOREIGN PATENT DOCUMENTS

| | | |
|---|---|---|
| 0151278 | 8/1985 | European Pat. Off. |
| 0170466 | 5/1986 | European Pat. Off. |
| 3401258 | 2/1994 | Germany |
| 0130193 | 10/1979 | Japan |
| 5232396 | 3/1997 | Japan |
| 0963794 | 7/1964 | United Kingdom |

Primary Examiner—Jill Warden
Assistant Examiner—Sharidan Carrillo

[57] ABSTRACT

Both a method and a kit for testing the fitness of a polyolester lubricant of the type used in a refrigerant compressor are provided. In the method of the invention, a solution for indicating an excess acidity of the polyolester lubricant is obtained by mixing a color acidity indicator, such as alizarin, with a sufficient amount of an alkaline to neutralize the inherent acidity of the lubricant. The resulting solution changes color only upon the presence of an excess acid condition associated with a compressor malfunction, such as burn out. Both the method and the kit are particularly well adapted to determine the fitness of polyolester lubricants of the type prepared by the reaction of trimethylolpropane with a mixture of a branched and a linear acid.

10 Claims, 1 Drawing Sheet

METHOD AND KIT FOR TESTING POLYESTER LUBRICANTS USED IN REFRIGERANT COMPRESSORS

BACKGROUND OF THE INVENTION

This invention generally relates to a method and kit for determining the fitness of a polyolester lubricant for use in a refrigerant compressor. More particularly, the invention relates to a method for determining excess acidity in such lubricants indicative of a compressor malfunction.

In refrigerant compressors, lubricants are generally added to the refrigerants in order to protect and prolong the life of the frictionally engaged compressor components. Presently, most refrigerants are fluorocarbon compounds such as CFCs and HCFCs. An example of such a chlorofluoro-carbon refrigerant is sold under the tradename R-12 by the DuPont Chemical Company located in Wilmington, Del. The lubricants commonly used with such CFC and HCFC refrigerants are chloronaphthenic oil and alkyl bezene oil.

With the legislative changes which prohibit the use of refrigerants having a high ozone depletion potential (ODP) or high global warming potential (GWP), the use of such CFC and HCFC refrigerants (such as R-12) will be banned in the near future. This in turn will necessitate the use of substitute refrigerants such as fluorinated hydrocarbons (HFC), examples of which are sold under the tradename R-134a and R-404a by the Dupont Chemical Company. The different chemistry of these substitute refrigerants requires the use of polyolester (POE) lubricants, since nephthenic oil and alkyl bezene oil are not compatible with such refrigerants.

It has long been observed that, when any serious type of mechanical malfunction of the compressor occurs (such as burn out), that the nephthenic and alkyl bezene oils used in the prior art will at least partially break down into organic acids. Accordingly, acid test kits have been developed for determining the acidity condition of such prior art lubricants. An acidity reading of above a certain mount indicates that the lubricant oil had broken down to such an extent as to render it unfit for further use within the compressor.

While such test kits have long been used successfully with prior art refrigerants lubricated by nephthenic and alkyl bezene oils, these kits give erroneous results when used with refrigerants lubricated by polyolesters, despite the fact that polyolester likewise break down into acidic compounds when exposed to burn out or other failing mechanical conditions (particularly in the presence of moisture). The applicants have observed that such erroneous results are caused by the inherent acidity of such polyolester lubricants. Specifically, while the nephthenic oil and alkyl bezene oils used in the prior art may have a TAN of near zero, the TAN for a polyolester lubricant is inherently higher. Hence the use of a prior art test kit on a refrigerant lubricated by a polyolester will invariably indicate that the lubricant is unfit for service even when the lubricant is highly fit.

Clearly, there is a need for a novel test kit that is capable of reliably determining the fitness of a polyolester lubricant in a refrigerant. Preferably, such a test kit should employ inexpensive acid indicators, and be simple and quick to use.

SUMMARY OF THE INVENTION

Generally speaking, the invention is both a method and a kit for testing the fitness of a polyolester lubricant for use in a refrigerant compressor. In the method of the invention, a solution for indicating an excess acidity of the polyolester lubricant is first prepared by mixing an acidity indicator with a sufficient amount of an alkaline to neutralize the inherent acidity of the lubricant. Next, the acidity indicating solution is mixed with a sample of the polyolester lubricant to be tested. Because the alkaline in the acidity indicating solution neutralizes the inherent acidity of the polyolester lubricant, the solution will indicate an acid condition only upon the presence of an excess acid condition of the type caused by a mechanical malfunction of the compressor, such as burn out.

In the preferred embodiment, the acidity indicator is a color indicator of one of the group consisting of methyl red, neutral red, meta-cresol purple, phenol red, m-nitrophenol, and alizarin. Because the inherent total acid number (TAN) of polyolester lubricants used in refrigerant compressors is higher than that of prior art lubricants, a sufficient amount of alkaline should be added into the acidity indicating solution to bring the TAN down to a value of zero. In the preferred embodiment, the alkaline used is an alkali hydroxide, such as KOH. While any one of organic solvents may be used to form the solution of alizarin and KOH, an alcohol such as methanol, is preferred since such a solvent is readily mixable with the polyolester being tested.

The kit of the invention includes one vessel containing 9.7 milliliters of 0.01% alizarin in methanol to which 0.3 milliliters of 10N KOH and methanol is added. Approximately 5 milliliters of the indicator solution is added to 5 milliliters of the polyolester lubricant sample to be tested. If the color of the indicating solution remains purple, no excess acidity is present, and the sample lubricant is satisfactory for use in the compressor. However, if the indicator solution turns either amber or yellow, an excess acid condition is indicated, and the lubricant is unfit for use in such compressor.

BRIEF DESCRIPTION OF THE SEVERAL FIGURES

DETAILED DESCRIPTION OF PREFERRED EMBODIMENT

Figure 1:
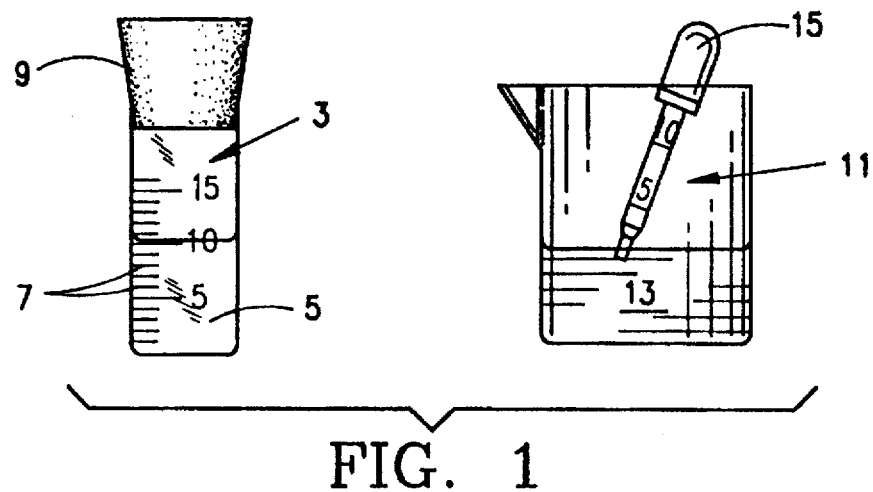
FIG. 1 illustrates the test kit of the invention.

The method and test kit of the invention is particularly adapted for use with polyolester (POE) lubricants of the type prepared by the reaction of a polyol such as trimethylolpropane with both a branched acid such as trimethyl hexanoic acid and a linear or minor acid such as heptanoic to decanoic acid. Such a lubricant is manufactured and sold under the tradename Solest-35 by CPI Engineering located in Midland, Mich. After the synthesis of such a polyolester lubricant, unreacted acids are removed by giving the polyolester a caustic wash. However, despite the caustic wash, some acidic groups remain attached to the polyolester molecules, giving them some acidic characteristics. Specifically, the total acid number or TAN of a newly manufactured polyolester lubricant is typically less than 0.1. Such a total add number brings the pH of a newly manufactured polyolester to a little less than 7.0.

Such polyester lubricants are particularly useful in refrigerant compressors that utilize environmentally acceptable HFC refrigerants such as R-134a and R-404a sold by the DuPont Chemical Company. Unlike the nephthenic oil and alkyl bezene oil used as lubricants in environmentally unacceptable CFC and HCFC refrigerants, such polyolester lubricants are readily miscible with R-134a and R-404a refrigerants, and serve to protect the moving parts inside the compressor from excess wear. However, when these particular lubricants are exposed to excessive heat due to a mechanical malfunction of the compressor, such as may occur in a burn-out condition, additional acids may be formed as a result of reactions between the polyolester and the refrigerant. Under a burn-out condition in the presence of moisture (which is almost always present at least in small quantities in the compressor) the polyolester lubricant can be converted into its precursor acids such as fatty acids. Accordingly, any significant increase in the acidity of the polyolester lubricant over a TAN of 0.6 or a Ph of under 7.0 indicates that a mechanical malfunction has occurred in the compressor of a magnitude sufficient to interfere with the ability of the lubricant to adequately lubricate the moving parts within the compressor.

The invention is both a method and a kit for determining the acidity of the polyolester lubricant in order to determine the fitness of the lubricant for continued service. The kit of the invention comprises a vessel containing a solution for indicating an acidity level of a polyolester lubricant beyond its aforementioned inherent acidity, and a further container for mixing the acidity indicating solution with a sample of lubricant. The excess acidity indicating solution includes a color changing acidity indicator with a sufficient amount of an alkaline to neutralize the inherent acidity of the polyolester lubricant so that any color change in the solution indicates a Ph of under 7.0. The color changing acidity indicator may be any one of a number of indicators, including (but not limited to) methyl red (p-dimethylaminoazobenzenecarboxylic acid), neutral red or toluylene red (3-amino-7-(dimethyl-amino)-2-methylphenazine monohydrochloride), metacresol purple (otherwise known as m-cresolsulfonphthalein), phenol red (otherwise known as phenolsulfonephthalein), or m-nitrophenol ($NO_2C_6H_4OH$), or alizarin (otherwise known as 1,2 dihydrodoxyanthraquinone). In the preferred embodiment, the excess acid indicating solution is formed by a mixture in the proportions of 10 milliliters of 0.01% alizarin in methanol to which 0.3 milliliter of 10N KOH and methanol is added. Of course, other metal hydroxides may be used in lieu of KOH, including either alkali metal hydroxides or alkali earth metal hydroxides.

While a 0.01% solution of alizarin and methanol is a preferred component of the excess acidity indicating solution, methanol solutions having an alizarin concentration of between about 0.001% and 0.05% may also be used. Additionally, while a molar concentration of 10N KOH and methanol is the other preferred component of the resulting solution, solutions between about 2.6% and 3.0% KOH and methanol may also be used.

With reference now to FIGS. 1 through 4, the kit 1 of the invention comprises a glass vessel 3 containing an acidity indicating solution 5. A volumetric scale 7 is conveniently applied along the vertical axis of the vessel 3 to assist the operator in mixing the proper proportions of acidity indicating solution 5, and a lubricant sample. The vessel 3 preferably includes a stopper 9 as shown. The kit 1 further comprises a second vessel 11 for confining a sample of a polyolester lubricant 13. An eyedropper 15 may optionally be included in the kit 1, to measure out 5 millimeters of sample lubricant, as may a calibrated color block 17 (shown in FIG. 4) for assisting the operator in determining the acidity associated with the particular color generated by the mixture of lubricant and acidity indicating solution 5.

Figures 2, 3:
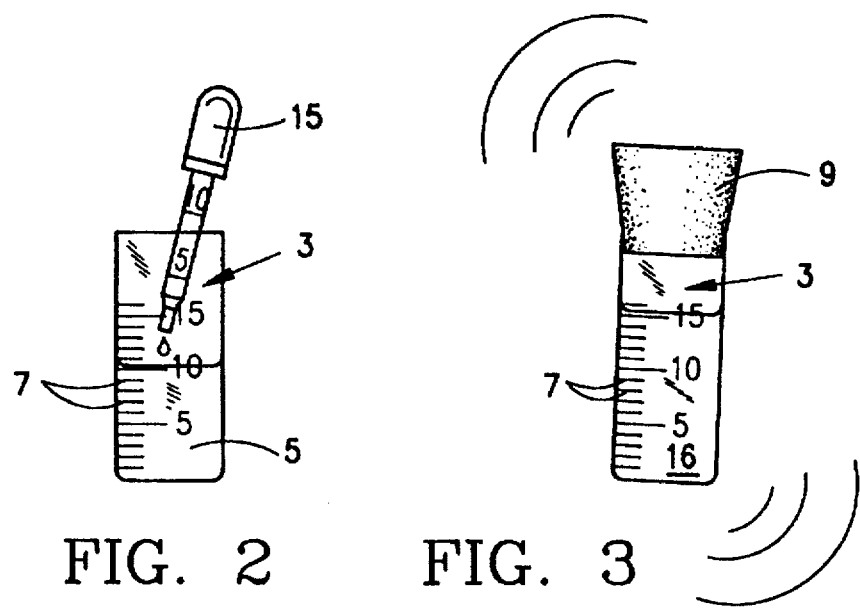
FIG. 2 illustrates the step in the method of the invention of adding 0.5 milliliters of sample lubricant to the acidity indicating solution.
FIG. 3 illustrates the step of mixing the lubricant with the acidity indicating solution, and FIG. 4 indicates the optional step of the method of comparing the color of the acidity indication solution with a set of calibrated colors.
Figure 4:
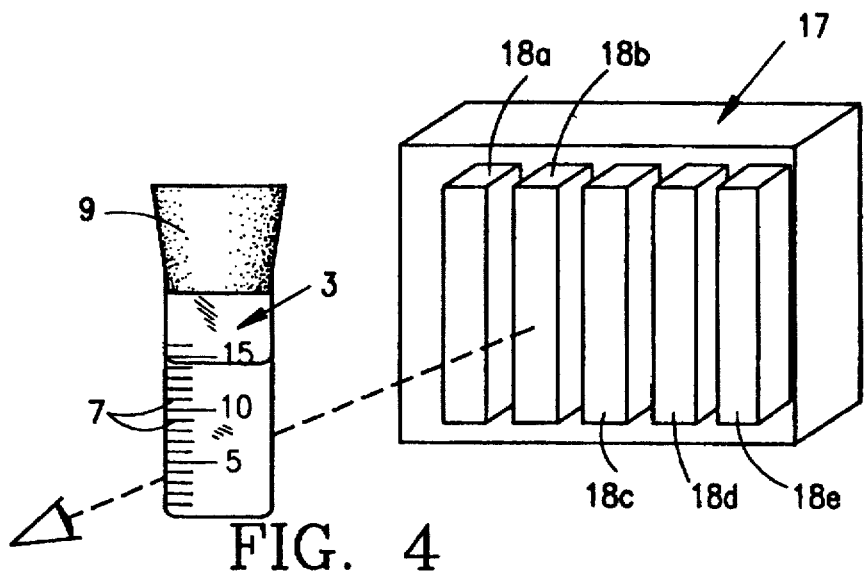

In the first step of the method of the invention, 9.7 milliliters of a 0.01% solution of alizarin and methanol is poured into the solution vessel 3. Next, 0.3 milliliters of 10N KOH and methanol is introduced into the vessel 3 in order to create 10.0 milliliters of an acidity indicating solution 5. As is indicated in FIGS. 1 and 2, 5 milliliters of lubricant sample 13 is withdrawn from the sample vessel 11 and introduced into the solution vessel 3. The stopper 9 is then returned to the vessel 3, and the resulting mixture 16 is shaken vigorously for approximately 15 seconds in order to homogeneously distribute the lubricant sample 13 throughout the acidity indicating solution 5. Finally, as is indicated in FIG. 4, the resulting color of the mixture 16 may be compared with calibrated color samples 18a–e contained within the calibrated color block 17 (which is preferably formed from transparent plastic).

The initial color of the excess acidity indicating solution 5 is purple. If the solution remains purple then there is no excess acidity in the sample 13 of polyolester lubricant, and the lubricant is fit for continued service. However, if the mixture 16 should turn amber colored, then a sufficiently acidic condition would have arisen within the lubricant so as to render it unfit for service. If the mixture 16 should turn yellow, then a highly acidic condition is indicated in the polyolester lubricant, and the lubricant is clearly unfit for further service.

The following table represents a variety of different test results arrived at through the kit and method of the invention:

| Lubricant | Acid Content | TAN Mg KOH/gm | Color | Condition As Per Test |
|---|---|---|---|---|
| POE Solest-35 | | 0.08 | Purple | OK, No Acid |
| POE Solest-35 | 0.1% branched acid | 0.42 | Light Purple | OK |
| POE Solest-35 | 0.2% branched acid | 1.02 | Amber | Acidic |
| POE Solest-35 | 0.3% branched acid | 1.26 | Amber | Acidic |
| POE Solest-35 | 0.5% branched acid | 1.5 | Amber-Yellow | Very acidic |
| POE Solest-35 Heated in high humidity[1] | — | 0.3 | Purple | OK. |
| POE Solest-35 Heated in high humidity[2] | — | 0.6 | Amber | Acidic |
| POE Solest-120 | 0.1% branched acid | 0.5 | Light Purple | OK |
| POE Solest-120 | 0.2% | 0.9 | Amber-Yellow | Acidic |
| POE Solest-120 | 0.3% branched acid | 1.8 | Yellow | Very Acidic |

[1] 4 hours at 80°
[2] 8 hours at 80° C.

Both the kit and method of the invention advantageously use a color metric acidity indicator whose color changing range has been reset by the addition of an alkaline substance therein, and whose strongly contrasting color changes within the reset range provide clear and unambiguous indications of acidity conditions which render the polyolester lubricant unfit for further service.

What is claimed:

1. A method for testing the fitness of a polyolester lubricant for use in a refrigerant compressor, said lubricant having a maximum acceptable total acid number (TAN) of 0.60, comprising the steps of:

a) obtaining a polyolester lubricant sample to be tested;

b) preparing a solution for indicating a total acid number in said polyolester lubricant of over 0.60 by mixing a color changing acidity indicator with a sufficient amount of alkaline to neutralize said maximum acceptable total acid number of 0.60 of said lubricant so that said indicating solution indicates an excess acidity condition of the polyolester lubricant by changing color only upon contact with said lubricant having a total acid number of 0.6 or greater;

c) mixing said indicating solution with a said lubricant sample to produce a reaction mixture;

d) observing the color of the reaction mixture; and e) determining the total acid number of 0.6 or greater if the indicating solution changes color and a total acid number of less than 0.6 if no color change occurs upon contact of the indicating solution with the lubricant in the reaction mixture, wherein a change in color indicates an excess acidity condition of the polyolester lubricant indicating that said lubricant is unfit for further service and wherein no color change is an indication of an acceptable acidity condition of the lubricant such that said polyolester lubricant is fit for use in the refrigerant compressor.

2. The method of claim 1, wherein said solution includes a mixture of alizarin, a metal hydroxide, and a solvent.

3. The method of claim 2, wherein said metal hydroxide is an alkali metal hydroxide, and said solvent is an alcohol.

4. The method of claim 3, wherein said metal hydroxide is KOH, and said solvent is methanol.

5. The method of claim 1, wherein said polyolester lubricant is prepared by the reaction of trimethylolpropane with branched and linear acids to create a polyolester having attached acidic groups which contribute to the total acid number of the resulting polyolester.

6. The method of claim 1, wherein said acidity indicator selected from the group consisting of methyl red, neutral red, meta-cresol purple, phenol red, m-nitrophenol, and alizarin.

7. A kit for testing the fitness of a polyolester lubricant for use in a refrigerant compressor, said lubricant having a maximum acceptable total acid number (TAN) of 0.60, comprising:

a) a solution for indicating a total acid number in said polyolester lubricant of over 0.60 including a mixture of an acidity indicator with a sufficient amount of alkaline to neutralize said maximum acceptable total acid number of 0.60 of said lubricant so that said indicator solution indicates an excess acidity condition of the polyolester lubricant by changing color upon contact with lubricant having a total acid number of 0.6 or greater, and wherein the excess acidity condition is an indication that said lubricant is unfit for further service and wherein no color change is an indication of a total acid number of less than 0.6 and an acceptable acidity condition such that said polyolester lubricant is fit for use in the refrigerant compressor; and b) a vessel for mixing said indicator solution with a sample of said polyolester lubricant.

8. The kit of claim 7, wherein said solution consists of a mixture of a color acidity indicator dissolved in a solvent and an alkaline dissolved in a solvent.

9. The kit of claim 8, wherein said solution consists of a mixture of alizarin in an alcohol and an alkali metal hydroxide dissolved in an alcohol.

10. A method for testing the fitness of a polyolester lubricant for use in a refrigerant compressor, said lubricant being prepared by the reaction of trimethylopropane with branched and linear acids to create a polyolester lubricant having acidic groups which are attached to the resulting polyolester, having a maximum acceptable total acid number (TAN) of 0.60, comprising the steps of:

a) obtaining a polyolester lubricant sample to be tested;

b) preparing a solution for indicating a total acid number in said polyolester lubricant of over 0.60 by mixing 9.7 milliliters of a 0.01% solution of alizarin in methanol with 0.3 milliliters of 10N KOH in methanol to create a color changing acidity indicator with a sufficient amount of alkaline to neutralize said maximum acceptable total acid number of 0.60 of said lubricant so that said indicating solution indicates an excess acidity condition of the polyolester lubricant by changing color only upon contact with said lubricant having a total acid number of 0.6 or greater;

c) mixing said indicating solution with a 5 milliliters of lubricant sample to produce a reaction mixture;

d) observing the color of the reaction mixture; and e) determining the total acid number of 0.6 or greater if the indicating solution changes color and a total acid number of less than 0.6 if no color change occurs upon contact of the indicating solution with the lubricant in the reaction mixture, wherein a change in color indicates an excess acidity condition of the polyolester lubricant indicating that said lubricant is unfit for further service and wherein no color change is an indication of an acceptable acidity condition of the lubricant such that said polyolester lubricant is fit for use in the refrigerant compressor.

* * * * *